Jan. 3, 1950 F. MEILLAND Plant Pat. 911
ROSE PLANT
Filed Oct. 6, 1948
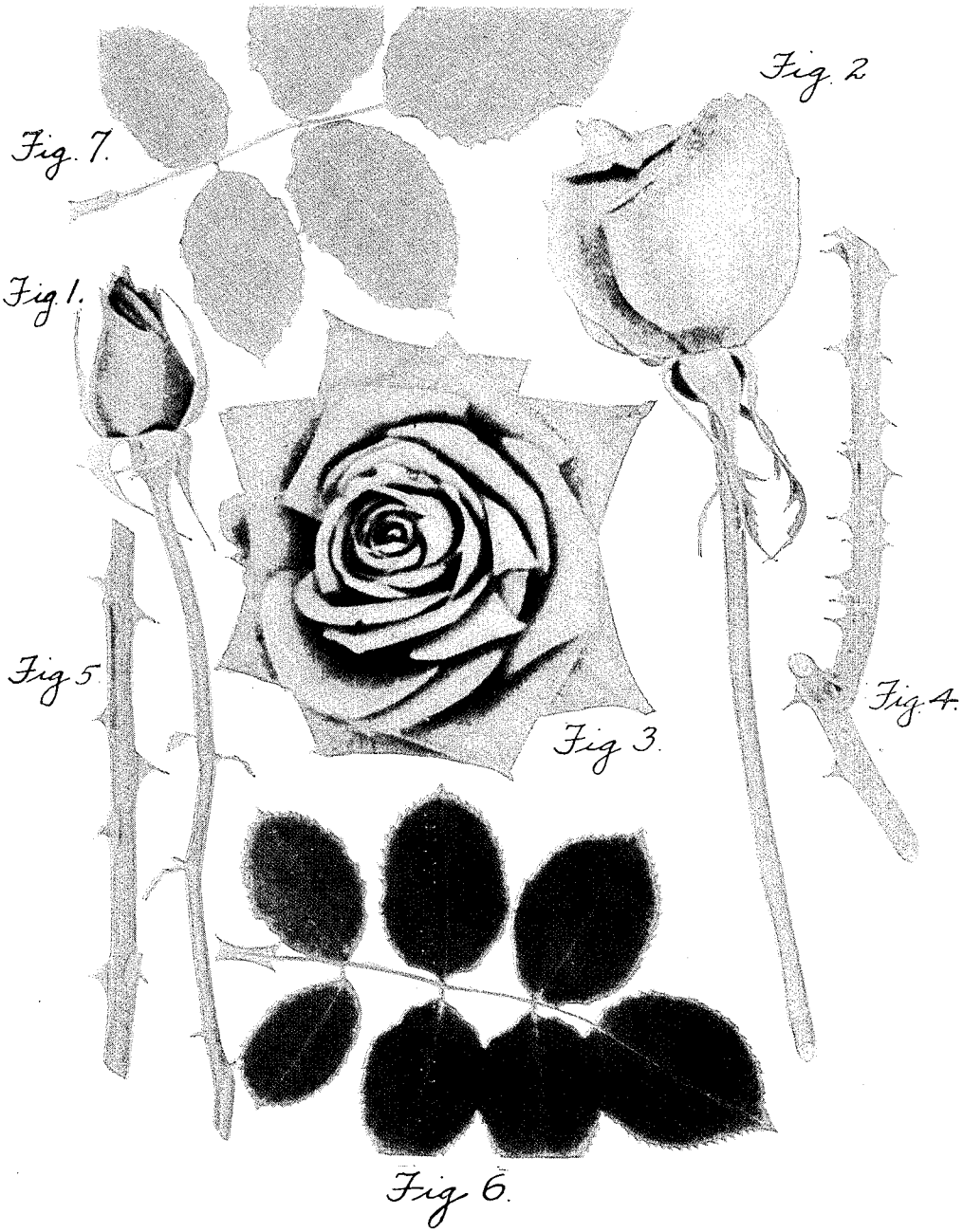
Inventor
F. Meilland
By Robb & Robb
Attorneys Patented Jan. 3, 1950

Plant Pat. 911

UNITED STATES PATENT OFFICE

911

ROSE PLANT

Francis Meilland, Cap Azura, Cap d'Antibes, France, assignor to The Conard-Pyle Company, West Grove, Pa., a corporation of Pennsylvania Application October 6, 1948, Serial No. 53,013

1 Claim. (Cl. 47—61)

This invention relates to a new and distinct variety of hybrid tea rose plant having as a primary objective of the crossing the production of a red variety of rose, incorporating therein qualities that make for excellence for greenhouse or underglass growing, as well as for garden use.

This new variety represents a marked distinction over present leading red roses in respect of:

(1) Extraordinary vigorousness of growth and length of stem.

(2) Greater abundance of petals.

(3) Beauty or excellence of form of the flowers in all stages from bud to full blown flower.

(4) Greater thickness and tougher texture of petals which results in a longer keeping characteristic; and (5) Vividness of color due to an unusual iridescent brilliance of its own.

These characteristics are especially important in cut flower use and careful comparative descriptions are hereinafter made of flowers grown both inside and outside.

In the drawing:

Figure 1 is a view of a specimen of the bud and stem, as the calyx breaks;

Figure 2 is a similar view of the blossom at the half open stage;

Figure 3 is a plan view of the fully open blossom;

Figure 4 is a detail view of a section of the main stem showing the characteristic of the thorns;

Figure 5 is a section of a branch of the main stem;

Figure 6 is a specimen of the leaflets showing the upper surface of the seven-leaflet group; and Figure 7 is a similar view of the under surfaces of a five-leaflet group.

The following is a detailed description of the new variety, all references to color being in accordance with Ridgway's Color Standards and Nomenclature, The Robert F. Wilson Horticultural Color Chart, and the Royal Horticultural Society's Color Chart:

Type: Bush; outdoor; greenhouse; seedling; for cut flowers and garden decoration.

Class: Hybrid tea.

Propagation: Holds its distinguishing characteristics through succeeding propagations by grafting and budding.

Parentage: (Rome Glory × Eassin) × [Charles P. Kilham × (Charles P. Kilham × Capucine Chambard)].

*Flower*

Localities where grown:

*In greenhouse.*—Richmond, Indiana.

*Outdoors.*—West Grove, Pennsylvania.

Flowers borne: Singly on strong long stems.

Quantity of bloom: Abundant outdoors.

Continuity: Continuous.

Fragrance: Slight.

Bud:

*Peduncle.*—In greenhouse—long; heavy; erect; stiff; medium green; few red thorns. Outdoors—medium length; medium heavy; erect; stiff; Parrot Green, Plate VI (Ridgway); medium rough; with few prickles, Orange Cinnamon, Plate XXIX (Ridgway).

*Before calyx breaks.*—Size—medium large. Form—in greenhouse—long; pointed, with a conspicuous neck; with foliaceous appendages on the surface of the bud; with much cut foliaceous parts extending beyond the tip of the bud equal to ¼ or more of its length. Outdoors—medium length; pointed; with foliaceous appendages on the surface of the bud; with slender cut foliaceous parts extending beyond the tip of the bud equal to ¾ or more of its length.

*As calyx breaks.*—Color—in greenhouse—underlying basic color of Oxblood Red overlaid with Carmine and with streaks of Victoria Lake, Plate I (Ridgway); basic color 824 Chrysanthemum Crimson overlaid with 00823 Oxblood Red and 00823/1 Oxblood Red (Wilson). (No color in the Wilson chart corresponds to the streaks represented by Victoria Lake in the Ridgway Chart.) Outdoors—Coral Pink, Plate XIII, to Pomegranate Purple, Plate XII (Ridgway).

*As first petal opens.*—In greenhouse—Size—large. Form—long; pointed. Color—outside surface: 822/2 Cardinal Red with slight streaks of 00823/1 Oxblood Red (Wilson); inside surface: 724 Rose Red (Wilson). (There is no color in Ridgway to correspond to these colors in the Wilson Chart.) Occasionally there are green streaks on inside of first petal, streaks yellow at the base fanning out at the top from yellow green to blue green. Outdoors — Size — medium. Form — medium length; pointed. Color—outside surface: Carmine, Plate I (Ridgway), to Crimson Carmine, Tone 4, page 159 (Royal); inside surface: Dark Crimson Carmine, Tone 4, page 159 (Royal). (There are no colors in Ridgway to correspond to these in the Royal Chart.)

Bloom: Size, when fully open—large; 5¾" to 6¼".

*Petalage.*—Very double; from 35 to 50 petals, arranged regularly.

*Form.*—In greenhouse—high center at first; petals, at first, very tightly rolled outward; remaining later, at maturity, very tightly rolled outward. Outdoors—high center at first; remaining high centered; petals, at first, tightly rolled outward; remaining later,at maturity, tightly rolled outward.

Petals: Leathery; with inside velvety and outside satiny.

*Shape.* — Outside — round. Intermediate—obovate. Inside—obovate.

The following description of a newly opened flower was made from a rose grown in a greenhouse in the month of April, at Richmond, Indiana:

*Color.—Outside petal*—outside surface: 824/3 Chrysanthemum Crimson; inside surface: 724 Rose Red overlaid with 824 Chrysanthemum Crimson. *Intermediate petal*—outside surface: 724/1 Rose Red; inside surface: 724 Rose Red. *Inner petal*—outside surface: Lighter than 824/3 Chrysanthemum Crimson and darker than 724 Rose Red; inside surface: Lighter than 824/3 Chrysanthemum Crimson and darker than 724 Rose Red (Wilson).

The following description of a newly opened flower was made from a rose grown outdoors in the month of August at West Grove, Pennsylvania:

*Color. — Outside petal* — outside surface: Crimson Carmine, Tone 4, fading to Crimson Carmine, Tone 1; inside surface: Dark Crimson Carmine, Tone 4. *Intermediate petal*—outside surface: Crimson Carmine, Tone 4; inside surface: Bright Reddish Purple, Tone 4, page 161. *Inner petal*—outside surface: Fuscin Red, Tone 4, page 160; inside surface: Bright Reddish Purple, Tone 4, page 160 (Royal).

The following description was made from a rose open for three days in a greenhouse in the month of April, at Richmond, Indiana:

*Color.—Outside petal*—outside surface: 824/3 Chrysanthemum Crimson; inside surface: 727 overlaid with dark velvet, base tip yellow surrounded by a white circle, then about ½" of 727/1, then 727 with velvet. *Inner petal*—outside surface: 724/3 Rose Red; inside surface: 724/2 Rose Red (Wilson).

The following description was made from a rose open for three days outdoors in the month of August, at West Grove, Pennsylvania:

*Color.—Outside petal*—outside surface: Light Rosolane Purple, Plate XXVI (Ridgway) to Crimson Carmine, Tone 3 (Royal); inside surface: Crimson Carmine, Tone 4 (Royal). *Inner petal*—outside surface: Crimson Carmine, Tone 4; inside surface Crimson Carmine, Tone 4 (Royal).

*General color effect.*—Newly opened flower—Crimson Carmine, Tone 4. Three days open—Dark Crimson Carmine, Tone 4 (Royal).

*Behavior.*—Petals drop off cleanly.

*Flower longevity.*—Cut roses grown outdoors, kept at living room temperatures—4 to 5 days in August.

*Reproductive organs*

Stamens: Occasionally fused with petaloids. In the greenhouse many; outdoors medium number. Arranged regularly about pistils.

Filaments:

*In greenhouse.*—Medium long, reddish; most with anthers.

*Outdoors.*—Medium length; Eugenia Red, Plate XIII (Ridgway); most with anthers.

Anthers:

*In greenhouse.*—Medium large, yellow; all open at once.

*Outdoors.* — Medium length; Ochraceous Orange, Plate XV (Ridgway); all open at once.

Pollen:

*In greenhouse.*—Abundant, gold.

*Outdoors.* — Abundant, Cadmium Yellow, Plate III (Ridgway).

Pistils:

*In greenhouse.*—Many.

*Outdoors.*—Medium number.

Styles:

*In greenhouse.* — Uneven; long, medium heavy, bunched.

*Outdoors.*—Medium length, medium heaviness, bunched.

Stigma:

*In greenhouse.*—White.

*Outdoors.*—Pale Orange Yellow, Plate III (Ridgway).

Ovaries: All enclosed in calyx.

Hips: Globular; Viridine Green to Parrot Green, Plate VI (Ridgway).

Sepals: Permanent; moderately long.

*In greenhouse.*—Curled.

*Outdoors.*—Spear-shaped.

Seeds: Outdoors—few; medium size.

*Plant*

Foliage:

*In greenhouse.*—Compound of 3, 5 or 7 leaflets; abundant; medium large; leathery.

*Outdoors.*—Compound of 3 or 5 leaflets; normal amount; medium large; leathery.

*Leaflets.*—Oval with apex acute; base round; margin simply serrate.

*Color.—Mature*—upper surface: Dark Cress Green, Plate XXX (Ridgway); under surface: Pois Green, Plate XLI (Ridgway). *Young* — upper surface: Glossy Calla Green, Plate IV (Ridgway), veiled with Mars Brown, Plate XV (Ridgway); under surface: Chestnut Brown, Plate XIV (Ridgway).

*Rachis.*—Medium heavy; upper side grooved; under side sparsely thorny in greenhouse, sparsely prickly outdoors.

*Stipules.—In greenhouse*—short, narrow; with short points turning out at an angle of less than 45°. Outdoors — medium width; medium points; turning out at an angle of less than 90°.

Growth:

*Habit.*—Upright; branched.

*Growth.*—Vigorous.

*Canes.*—Moderately heavy.

*Main stems.*—Dull green. *Thorns*—many; medium length; straight; with long, broad base; incipient thorns among large thorns. *Prickles and hairs*—none.

*Branches.* — *In greenhouse* — thorns — several; medium long; hooked downward; with long narrow base. *Outdoors*—Color—Grass Green, Plate VI (Ridgway). Thorns—several; medium long; slightly hooked downward; with a narrow base. Prickles few and hairs none.

*New shoots.*—*Color*—Calla Green, Plate V (Ridgway). Thorns — many; medium length; straight; with a narrow base. Prickles and hairs—none.

I claim:

A new and distinct variety of rose plant characterized as to novelty by its vigorous growth; length of stem; abundance of petals; excellence of form of flowers at all stages of development; thickness and tough texture of the petals; long lastingness of the blooms; and vivid iridescent brilliance of red color, substantially as shown and described.

FRANCIS MEILLAND.

(No references cited.)